United States Patent [19]

Montgomery

[11] 4,269,184
[45] May 26, 1981

[54] SILICONE TRACHEAL CANNULA

[76] Inventor: William W. Montgomery, 243 Charles St., Boston, Mass. 02114

[21] Appl. No.: 125,260

[22] Filed: Feb. 28, 1980

[51] Int. Cl.³ ............................................ A61M 25/00
[52] U.S. Cl. ............................ 128/207.14; 128/200.26
[58] Field of Search ...................... 128/207.14, 200.26, 128/207.17

[56] References Cited

U.S. PATENT DOCUMENTS

| | | | |
|---|---|---|---|
| 3,137,299 | 6/1964 | Tabor | 128/207.16 |
| 3,263,684 | 8/1966 | Bolton | 128/207.16 |

FOREIGN PATENT DOCUMENTS

| | | |
|---|---|---|
| 3273 of 1899 | United Kingdom | 128/200.26 |
| 28726 of 1913 | United Kingdom | 128/200.26 |

Primary Examiner—Henry J. Recla
Attorney, Agent, or Firm—William R. Hulbert

[57] ABSTRACT

A tracheal cannula adapted to be inserted in a round incision in the patient's trachea in place of the usual tracheotomy tube, comprises a silicone tube about 6 cm. in length having a lumen of a diameter of the order of 8 mm. The cannula has preferably three circumferential barbs near its inner end to engage the patient's tissue and prevent outward displacement, a number of circumferential ridges located between the barbs and the outer end, and an inner open end whose periphery lies in a plane at an acute angle to its longitudinal axis. The inner end has a flange adapted to fit the inner anterior tracheal wall so that the cannula will project forward at a predetermined angle to the patient's neck. The circumferential ridges serve to retain an apertured plate or washer for engaging the patient's skin surrounding the cannula to secure the latter in place.

10 Claims, 8 Drawing Figures

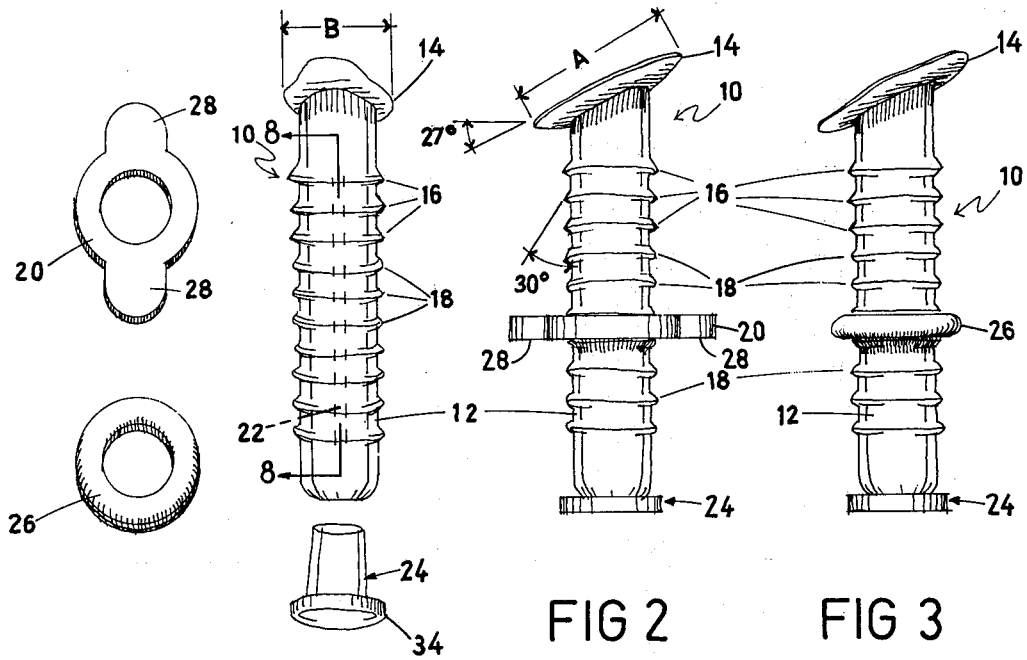

SILICONE TRACHEAL CANNULA

BACKGROUND OF THE INVENTION

The first mention of a tracheotomy tube is in the writings of Fabricius in the sixteenth century. He described this tube as small, straight and short with two wings at the outer end to prevent the tube from sliding into the trachea.

Dailio Casserio, a pupil of Fabricius, described a curved tube with several holes in its lower portion for air. The curved (quarter circle) tube has been in use since that time.

In the early eighteenth century the idea was introduced of using an inner tube to keep the tracheotomy tube clear of mucus without removing the outer tube from the trachea.

In the middle nineteenth century many modifications were made on the tracheotomy tube. The most popular tube in use today is the Tucker metal tracheotomy tube. There have been many tracheotomy tubes and "buttons" which extend only to the tracheal wall and do not project into the trachea. The tracheal cannula of the invention is believed to be the first successful tracheotomy tube which does not project into the lumen of the trachea.

SHORT STATEMENT OF THE INVENTION

The object of the invention is to provide a novel tracheal cannula, adapted to replace the usual tracheotomy tube, which has not only all the advantageous features thereof but which is compatible with body tissue, readily inserted, is free of any portions projecting into the lumen of the trachea, and which may serve, if need be, as a permanent airway provided with a removable plug to close it off when not needed.

In accordance with the invention, I provide a tracheal cannula adapted to be inserted in a round incision in the patient's trachea in place of the usual tracheotomy tube, the novel cannula comprising a tube of tissue-compatible material having a lumen of diameter sufficient to provide an adequate airway for the patient after insertion and an outer diameter adapted to fit the incision. The tube has at least one and preferably three circumferential barbs near its inner end adapted to engage the patient's tissue within the incision to discourage accidental outward displacement, a plurality of circumferential ridges located anteriorly of the barbs, and an inner open end whose periphery lies in a plane at an acute angle to the longitudinal axis of the tube and is surrounded by a flexible flange also lying in the same plane which may be flexed to a smaller diameter to permit insertion through the incision. The flange is adapted to fit the inner anterior tracheal wall so that the cannula will project forward at a predetermined angle to the patient's neck. The circumferential ridges are adapted to receive and retain means for engaging the patient's skin surrounding the cannula to secure the latter in place.

In a preferred embodiment, the inner open end lies in a plane at an angle of about 27° to the longitudinal axis of the tube; the vertical dimension of the flange is greater than its horizontal dimension to facilitate insertion and to prevent rotation of the cannula when it is in place; the means for engaging the patient's skin comprises a wing-shaped apertured plate fitting over the tube between and held by a pair of the ridges, the wings thereof being adapted to be sutured in place; a suture free washer may be subsequently substituted for the plate to cooperate with the inner flange to grip the patient's tissue therebetween and retain the cannula in place; a removable plug is provided for the outer end of the tube; the plug is provided with a portion larger than the inner diameter of the tube to limit its insertion into the tube.

In a specific presently preferred embodiment, the tube of the novel cannula is made of silicone and is about 6 cm. in length and has a lumen 8 mm. in diameter and an outer diameter of 10 mm. which will fit nicely in an 8 mm. round window in the patient's trachea; the tube is provided with three circumferential barbs near its inner end, which are roughly triangular in shape and slope outwardly at 30° to the axis of the tube, and seven anterior ridges; the plane of the inner open end and its surrounding flange is at exactly 27° to the tube axis, and the removable plug has a friction fit with the interior of the open outer end of the tube.

Further objects, features and advantages of the invention will become apparent from the following detailed description of a preferred embodiment taken in conjunction with the accompanying drawings.

DESCRIPTION OF THE DRAWINGS

FIG. 1 is a plan view of the disassembled several parts of the novel cannula;

FIG. 2 is a side view of the cannula revolved 90° from the position shown in FIG. 1 and with a wing-shaped apertured retaining plate thereon;

FIG. 3 is a view similar to FIG. 2 showing a retaining washer substituted for the wing-shaped plate;

FIG. 4 is a fragmentary perspective view showing the insertion of the cannula through an incision of the trachea of a patient;

FIG. 5 is a view similar to FIG. 4 showing the cannula after insertion and before the incision is closed;

FIG. 5A is a fragmentary detail, in section, showing the snug fit of the flange at the inner end of the cannula against the anterior intralumenal tracheal wall.

FIG. 6 is an elevation showing the cannula after the incision is closed, retained by the wings of the wing-shaped plate sutured to the patient's skin;

FIG. 7 shows the final condition of the cannula after the patient's wound has healed, a retaining washer having been substituted for the plate and a removable plug blocking the open end of the cannula; and FIG. 8 is a vertical section on line 8—8 of FIG. 1 illustrating the difference between the profiles of different ridges on the surface of the cannula.

DETAILED DESCRIPTION OF PREFERRED EMBODIMENT

The novel tracheal cannula, indicated generally by the numeral 10, is intended to be used in place of a tracheotomy tube. The main advantage is that there is no foreign body projecting into the trachea as the cannula extends only to the inner surface of the anterior tracheal wall. The cannula is constructed from vulcanized silicone material to which there is no tissue reaction. The cannula comprises a tube or shaft 12 of outside diameter 10 mm. and inside diameter of 8 mm. which provides an adequate airway for both male and female adults of all ages, and about 6 cm. long. The silicone tracheal cannula includes an inner flange 14 which, when inserted, fits against the contour of the inner anterior tracheal wall. This inner flange 14 is thin, shaped so as to conform to the inner aspect of the anterior tracheal wall and is designed so that the vertical dimension A is greater than the horizontal dimension B. This allows for ease of insertion into the opening of the anterior tracheal wall and also prevents rotation of the cannula once it is in place.

The inner flange 14 is fashioned at a 27° angle to the long axis of the tube 12 so that the cannula will project straight forward or in a slightly superior direction when in place (FIGS. 5, 6, and 7). There are ten circumferential ridges on the shaft of the tracheal cannula. The three inner ridges 16 are roughly triangular in shape (FIGS. 2 and 8) to define circumferential barbs angled at about 30° to the long axis. This allows the tracheal cannula to be easily inserted but prevents it from being anteriorly displaced once the cannula is fixed in place. The seven outer ridges 18 are rounded (FIG. 8). The grooves between these latter ridges serve to secure the apertured face plate 20, described below, in the desired position according to the thickness of the wall between the trachea and anterior cervical skin. There is a groove 22 along the inferior surface of the shaft of the silicone tracheal cannula which serves not only to allow the drainage of serum and products of inflammation which may occur during the immediate post-operative period but also to identify readily the inferior aspect of the tube. As such, it is a point of reference to indicate if the inner flange 14 has been accidentally rotated out of its proper position.

The silicone tracheal cannula set also includes, in addition to a wing-shaped apertured face plate 20, a plug 24, and a ring washer 26. The wing-shaped face plate serves to secure the cannula in place at the time of surgery by suturing the wings 28 to the skin 30 of the patient by sutures 32 (FIG. 6). It is secured with 3-0 polyethylene suture material. The plug 24 is used to obstruct the cannula when the cannula airway is not needed. It has a friction fit and is secured in place by simply inserting and twisting it in a clockwise direction. The plug 24 has an enlarged head 34 so that it cannot be introduced too far into the tracheal cannula. This also facilitates manipulation for its insertion and removal. After the silicone tracheal cannula has been in place for a few weeks, the wing-shaped face plate 20 can be replaced by the ring washer 26 (FIG. 7). The washer is less bulky and prevents irritation of the skin surrounding the cannula. The 27° angle of the flange 14 is the end result of studying the angular relationship between the trachea and plane of the anterior cervical skin using soft tissue X-rays of 100 larynges and cervical tracheas.

METHOD OF INSERTION

Either a vertical or a horizontal skin incision (FIG. 4) can be made to insert the silicone tracheal cannula. I prefer the vertical incision be made with an electrical knife. The median raphe between the sternohyoid and sternothyroid muscles is identified and incised. The thyroid isthmus is divided and suture ligated at 36 (FIG. 4). The anterior wall 38 of the trachea is exposed so that the fenestration can be made at the proper level.

The fenestration of the anterior tracheal wall is made, preferably with the suction trephine knife, which is the subject of my co-pending application of even date, which cuts a perfectly round window of desired diameter.

To insert the end of the silicone tracheal cannula 10 into the trachea, its end including flange 14 is compressed using a curved hemostat 40 (FIG. 4). In so doing, this end forms a point which can easily be inserted into the lumen of the trachea. The tracheotomy cannula is then pulled anteriorly so that the inner flange fits snugly against the intraluminal anterior tracheal wall. The wound is closed in layers above and below the silicone tracheotomy cannula. The face plate 20 then is applied over the tracheotomy shaft 12 and advanced so that it fits fairly close but not too tightly against the skin 30 (FIG. 6). One non-absorbing suture 32 is placed on each wing 28 of the face plate 20 to secure it to the skin (FIG. 6). Anesthesia or oxygen can be administered by way of the tracheal cannula as the patient recovers from general anesthesia. If there is a significant loss of air superiorly into the upper respiratory system or if anesthesia is to be continued, then a Fogarty catheter is inserted and inflated superior to the level of the tracheal fenestration.

POST-OPERATIVE CARE

The face plate 20 is left in place for about ten days to two weeks until the silicone tracheotomy cannula is secure in place. It is advisable to clean under the face plate twice a day with either peroxide solution or betadine solution.

The small silicone ring or washer 26 replaces the face plate when it is removed (FIG. 7). This ring prevents medial displacement of the tube 12 and is much less irritating to the skin surrounding the tracheotomy as compared to the face plate. The shaft 12 can be shortened to a convenient length, as shown in FIG. 7, by cutting with straight scissors.

The silicone tracheal cannula can be plugged when it is not needed to assist or replace the upper airway. The plug 24 is inserted with a twist and will remain in place by friction. A silk suture can be placed through the plug and around the neck to prevent its being lost when not in use.

Post-operatively, a lateral soft tissue X-ray, preferably a xeroradiograph, of the larynx and trachea is obtained to make certain that the inner flange is in the proper position and firmly against the inner aspect of the anterior tracheal wall.

While I have herein disclosed and described a presently preferred embodiment of the invention, it is to be understood that such is not by way of limitation and the scope of the invention is to be measured by the appended claims.

I claim:

1. A tracheal cannula adapted to be inserted in a round incision in the patient's trachea in place of the usual tracheotomy tube, said cannula comprising a tube of tissue-compatible material having an outer open end, an inner open end and a lumen of diameter sufficient to provide an adequate airway for the patient after insertion and an outer diameter adapted to fit said incision, said tube having at least one circumferential barb near its inner end adapted to engage the patient's tissue within the incision to discourage accidental outward displacement after insertion, a plurality of circumferential ridges located between the outermost of said barbs and its outer open end, and said inner open end having a periphery which lies in a plane at an acute angle to the longitudinal axis of said tube and is surrounded by a flexible flange also lying in said plane, said inner end being capable of being flexed to a smaller diameter to permit insertion throught the incision, said flange being adapted to fit the inner anterior tracheal wall so that the cannula will project forward at a predetermined angle to the patient's neck, said circumferential ridges defining grooves adapted to receive and retain means for engaging the patient's skin surrounding the cannula to secure the latter in place.

2. The combination as claimed in claim 1 wherein said inner open end lies in a plane at an angle of about 27° to the longitudinal axis of said tube.

3. The combination as claimed in either claim 1 or claim 2 wherein the vertical dimension of said flange is greater than its horizontal dimension to facilitate insertion and to prevent rotation of the cannula when it is in place.

4. The combination as claimed in either claim 1 or claim 2 including said means for engaging the patient's skin surrounding the cannula to secure it in place.

5. The combination as claimed in claim 4 wherein said means for engaging the patient's skin comprises a wing-shaped apertured plate fitting over said tube in a groove between a pair of said ridges, the wings thereof being adapted to be sutured in place.

6. The combination as claimed in claim 4 wherein said means for engaging the patient's skin comprises a suture-free washer fitting over said tube between and held in a groove between a pair of said ridges and cooperating with said flexible flange to grip the patient's tissue therebetween and retain the cannula in place.

7. The combination as claimed in claim 4 including a removable plug for the outer end of said tube.

8. The combination as claimed in claim 7 wherein said plug and said outer end are provided with cooperating means for securing said plug removably in place and wherein said plug is provided with a portion larger than the inner diameter of said tube to limit its insertion in said tube.

9. The combination as claimed in either claim 1 or claim 2 wherein said circumferential barbs are roughly triangular in shape and slope outwardly at an angle of about 30° to the long axis of the tube.

10. The combination as claimed in claim 9 wherein said circumferential barbs are three in number.

* * * * *